United States Patent [19]

LaBella et al.

[11] Patent Number: 5,144,017
[45] Date of Patent: Sep. 1, 1992

[54] COMPOUNDS THAT BIND TO DIGITALIS RECEPTOR

[75] Inventors: Frank S. LaBella, Oakbank; John F. Templeton, Winnipeg, both of Canada

[73] Assignee: University of Manitoba, Winnipeg, Canada

[21] Appl. No.: 462,234

[22] Filed: Jan. 9, 1990

Related U.S. Application Data

[63] Continuation-in-part of Ser. No. 379,191, Jul. 13, 1989, abandoned.

[30] Foreign Application Priority Data

Jul. 13, 1988 [GB] United Kingdom ............... 8816619
Dec. 12, 1988 [GB] United Kingdom ............... 8828974
May 5, 1989 [GB] United Kingdom ............... 8910332

[51] Int. Cl.$^5$ .................... C07J 5/00; A61K 31/705
[52] U.S. Cl. .................................... 536/5; 536/4.1
[58] Field of Search ................... 536/5, 4.1; 514/26, 514/169

[56] References Cited

U.S. PATENT DOCUMENTS

| | | | |
|---|---|---|---|
| 3,740,390 | 6/1973 | Heider et al. | 536/5 |
| 3,752,803 | 8/1973 | Eberlein et al. | 536/5 |
| 3,857,832 | 12/1974 | Hartenstein et al. | 536/5 |
| 3,907,776 | 9/1975 | Eberlein et al. | 536/5 |
| 3,949,074 | 4/1976 | Eberlein et al. | 536/5 |
| 4,031,212 | 6/1977 | Lösel et al. | 536/5 |
| 4,088,757 | 5/1978 | Peterson | 536/5 |
| 4,242,332 | 12/1980 | Albrecht et al. | 536/5 |
| 4,380,624 | 4/1983 | Wiesner et al. | 536/5 |
| 4,895,836 | 1/1990 | Chiodini et al. | 514/26 |

FOREIGN PATENT DOCUMENTS 0765687 10/1971 Belgium .
2136036 2/1973 Fed. Rep. of Germany .
87/04166 7/1987 World Int. Prop. O. .

OTHER PUBLICATIONS

Brown et al; Naunyn–Schmiedeberg's Archives of Pharmacology 332:98–102 (1986).
Lucas et al; J. Am. Chem. Soc. 82:5688–5693 (1960).
Chow et al; Br. J. Pharmac. 67:345–352 (1979).
Kim et al; Molecular Pharmacology 18:402–405 (1980).
LaBella et al; Can. J. Physiol. Pharmacol. 62:1057–1064 (1984).
LaBella et al; Nature 278:571–573 (Apr. 5, 1979).
Brown et al; Arz Neim.–Forsch./Drug Res. 31(II), No. 7: 1059–1064 (1981).
LaBella et al; Fed. Proc. (FASEB) 44(12):2806–2811 (1985).
"Endogenous Digitalis: Current Status and Progesterone Derivatives as Candidates" by LaBella et al Proc. West. Pharmacol. Soc. 30:365 to 371 (1987).
"Progesterone Derivatives that Bind to the Digitalis Receptor: Synthesis of 14-Hydroxyprogesterone" by Templeton et al, J. Med. Chem. 1987, 30, 1502 to 1505.
"14-Hydroxyprogesterone Binds to the Digitalis Receptor, Inhibits the Sodium Pump and Enhances Cardiac Contractility" by Bose et al, Br. J. Pharmacy, 93:453 to 461 Feb. 1988.
"Structure-Activity-Relationships of Progesterone Derivatives that Bind to the Digitalis Receptor: Modifications in A and B Rings" by Templeton et al, Steroid, May–Jun. 1987 Ed. (pub. Apr. 1988).
"Digitalis–like Pregnanes Cardiac and Renal Effects of a Glycoside of 14β-Hydroxyprogesterone" by Templeton et al, Can. J. Physical. Pharmacol., 66, 1420 to 1428 (1988).
"Cardiac Glycoside-like Structure and Function of 5β, 14β-Pregnanes" by Templeton et al, J. Med. Chem., 32, 1977 to 1981 (1989).
Weiland et al in J. Enz. Inhib. 2:31 to 36, 1987.
The Pharmacologist, 29:135, (1987), Halpryn et al.

*Primary Examiner*—Johnnie R. Brown
*Assistant Examiner*—Nancy S. Carson
*Attorney, Agent, or Firm*—Sim & McBurney

[57] ABSTRACT

Novel steroid compounds which are glycoside derivatives of 14β-hydroxypregnane and 17α-acetoxy-6α-methylpregnane are described. The compounds have increased receptor potency when compared to their aglycone and beneficial renal effects.

2 Claims, 8 Drawing Sheets

$5\alpha, \Delta^4, \Delta^5, 14\alpha, \Delta^{14}$ $5\beta, 14\alpha, \Delta^{14}$ $5\alpha, \Delta^4, \Delta^5, 14\beta$ $5\beta, 14\beta$

TABLE
Relative Potencies of Progesterone Derivatives in a $^3$H-Ouabain RBA

| | | R | R' | IC$_{50}$ (uM) | | | R | R' | IC$_{50}$ (uM) |
|---|---|---|---|---|---|---|---|---|---|
| I | a | H | | 93 | II | a | H | H | 42 |
| | b | F | | 49 | | b | F | H | 55 |
| | c | Cl | | 3 | | c | Cl | H | 62 |
| | d | Br | | 2 | | d | CH$_3$ | H | 8 |
| | e | CH$_3$ | | 12 | | e | OAc | H | NA |
| | f | =O | | 148 | | f | OH | H | NA |
| | g | OCH$_3$ | | 160 | | g | H | Ac | 78 |
| | h | OC$_2$H$_5$ | | NA | | h | CH$_3$ | Ac | 43 |
| | i | OCOOCH | | NA | | i | OAc | Ac | NA |
| | j | OAc | | NA | | j | OH | Ac | NA |
| | k | OH | | NA | | k | =O | Ac | NA |
| | l | β-Cl | | NA | | l | CH$_3$ | α-OH | 66 |
| | m | β-Br | | 87 | | m | CH$_3$ β-D-glucoside | | 3.6 |
| III | a | H | | 59 | IV | a | Cl | H | 3 |
| | b | CH$_3$ | | 4 | | b | CH$_3$ | H | 10 |
| | c | Cl | | 0.5 | | c | Cl | Ac | 4 |
| | d | Br | | 1 | | d | CH$_3$ | Ac | 115 |
| | | | | | | e | CH$_3$ β-D-glucoside | | 16 |
| V | a | =O | | NA | VI | a | H | | NA |
| | b | OH | | NA | | b | CH$_3$ | | NA |
| | c | OAc | | NA | | c | OAc | | NA |
| | | | | | | d | OH | | NA |
| VII | a | OAc | H | NA | VIII | a | CH$_3$ | H | NA |
| | b | OH | H | NA | | b | OH | H | NA |
| | c | CH$_3$ | H | 59 | | c | =O | Ac | NA |
| | | | | | | d | β-OH | Ac | NA |
| | | | | | | e | OAc | H | NA |
| IX | a | H | H | NA | X | a | H | H | NA |
| | b | CH$_3$ | H | 200 | | b | CH$_3$ | H | 27 |
| | c | H | Ac | 138 | | c | H | Ac | NA |
| | d | CH$_3$ | Ac | 95 | | d | CH$_3$ | Ac | NA |
| | e | OAc | Ac | 37 | | e | OAc | Ac | NA |
| XI | a | H | H | NA | XII | a | (α-epoxide) | | NA |
| | b | CH$_3$ | H | NA | | b | (β-epoxide) | | NA |
| | c | H | Ac | NA | | | | | |
| | d | CH$_3$ | Ac | NA | | | | | |

FIG. 4.

COMPOUNDS THAT BIND TO DIGITALIS RECEPTOR

REFERENCE TO RELATED APPLICATION

This application is a continuation-in-part of copending U.S. patent application Ser. No. 379,191 filed Jul. 13, 1989, now abandoned.

FIELD OF INVENTION

The present invention relates to certain novel steroid compounds which exhibit novel effects which suggest utility as heart stimulants.

BACKGROUND TO THE INVENTION

The digitalis-derived steroid glycosides have been among the most widely-prescribed drugs. Digoxin today is the most favored digitaloid in the clinic and is extensively used to treat certain cardiac dysfunctions. The cardiac glycosides bind with high affinity and high specificity to a $Na^+$- and $K^+$-transporting ATPase. It is generally accepted that inhibition of this cellular enzyme by the cardiac glycosides initiates a series of events in the cardiac muscle that lead to increased contractility.

Weiland et al in J. Enz. Inhib. 2:31 to 36, 1987 have described the effect of forming glycosides of chloramidone acetate (CMA). It had previously been observed that CMA had a high affinity for Na/K-ATPase but causes cardiodepression or decreased contractility, which overrides any positive effects on contractility that otherwise result from inhibition of the $Na^+/K^+$ pump. Certain glycoside derivatives of CMA, namely the arabinofuranoside and the rhamnoside derivatives, are described by Weiland et al and were tested for $Na^+/K^+$-ATPase inhibition and in vivo inotropic activity, in comparison with the hydroxy derivatives of CMA and digoxin.

A decreased potency for the glycosides was observed when compared to the hydroxy derivative of CMA and digoxin (itself a glycoside) but the glycosides increased contractility, in comparison with the depressive action of CMA. High doses of the glycoside did not induce arrhythmias, in contrast to the effect of digoxin at high dose levels.

In a publication in The Pharmacologist, 29:135, (1987), Halpryn et al, there is described the provision of another glycoside derivative of a pregnane, namely 3β-rhamnosyloxy-14β-amino-5β-pregnane-20β-ol. The effect on cardiac contractility of this compound and digoxin were compared and the new compound was found to be superior, in terms of tolerance to higher dosage. This compound is as potent as the cardiac glycosides, as disclosed by Schonfeld et al, Arch. Pharmacol. 329:414-426, 1985.

An extensive study has been conducted by the inventors with respect to a wide series of steroids of the pregnane and androstane type. The potencies of these steroids were determined in a $^3H$-ouabain radioligand binding assay (RBA). Past experience has indicated to the inventors that the potency of the steroids to displace the labelled cardiac glycoside (i.e. ouabain) in the assay parallel their biological activity, that is their cardiac glycoside-like activity in the ability to inhibit Na/K-ATPase and elicit characteristic cellular response.

BRIEF DESCRIPTION OF DRAWINGS

FIG. 4 is a table of data showing the relative potencies as determined in a $^3H$-ouabain RBA for the compounds shown in FIG. 3.

SUMMARY OF INVENTION

Figure 1A:
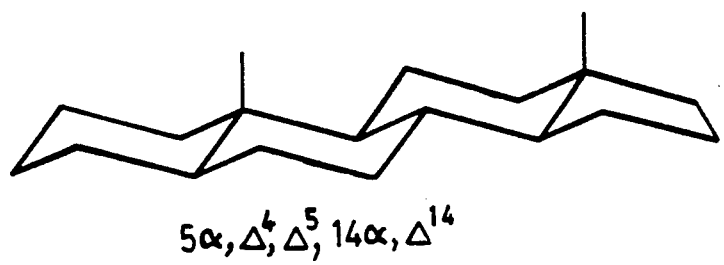
FIGS. 1a to 1d is a side view of the basic steroid ring structure for the various steroids which form the subject of this invention in the various steric configurations of the rings.
Figure 1B:
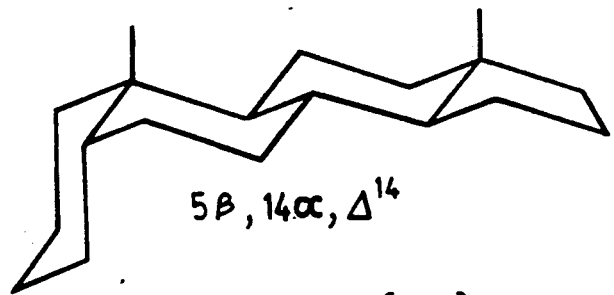
Figure 1C:
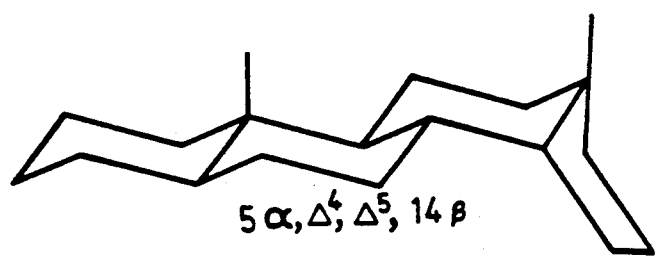
Figure 1D:
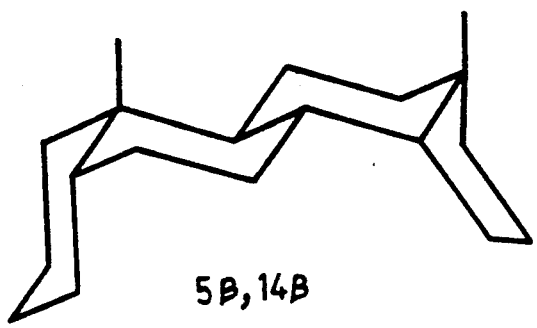

In accordance with the present invention there are provided novel glycoside derivatives of steroids exhibiting enhanced receptor potency as well as enhanced cardiac contractility. These novel steroid compounds all have a ring structure, as follows:

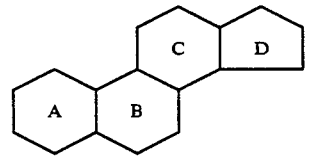

Four stereo isomers of this ring structure can exist, as seen in FIGS. 1a to 1d. The first structure (a) is a planar one, in which the stereochemistry of the A/B ring junction is trans (5α) or there is unsaturation at $C_4$ or $C_5$ ($\Delta^4$, $\Delta^5$) and the C/D ring junction is trans (14α) or there is unsaturation at $C_{14}$ ($\Delta^{14}$). The second structure (b) is a bent structure in which the A/B rings are cis (5β) and the C/D rings are trans or have unsaturation at $C_{14}$ ($\Delta^{14}$) The third structure (c) is a bent structure in which the C/D rings are cis (14β) and the A/B ring junction is trans (5α) or there is unsaturation at $C_4$ or $C_5$ ($\Delta^4$, $\Delta^5$), and the fourth structure (d) is a doubly-bent structure in which both A/B and C/D rings are cis (5β,14β).

The prior art referred to above has described compounds of these general types. The glycosides of CMA described by Weiland et al are of the first type of structure. As noted earlier, Weiland et al disclosed that glycosylating the CMA decreased potency and increased the cardiac contractility as well as showing an improved tolerance to higher dosage levels. In one aspect of the present invention, it has been found that, if the chlorine substituent in the B ring is replaced by an α-methyl group, the corresponding glycoside derivatives exhibit improved potency and are expected to exhibit the same increased cardiac contractility and tolerance to higher dosage levels as reported by Weiland.

The Halpryn et al work is on steroids of the fourth type. In another aspect of the present invention, there are provided steroids having the first, second, third and fourth type of ring structure which exhibit, by selection of specific ring constituents, receptor potency, as well as their glycoside derivatives, which are expected to exhibit increased cardiac contractility and tolerance to high dosage levels.

The present invention is concerned with compounds in which the C/D rings are cis and wherein a hydroxy group is present at the 14β-position or in which both the A/B and C/D rings are trans, and wherein an α-methyl group is present at the 6-position and an α-acetoxy group is present at the 17- position. These compounds, therefore, are distinguished from those disclosed in the prior art, in that, as compared with Weiland et al, the structure either has a cis C/D ring junction or an α-methyl group at the 6-position and, as compared with Halpryn et al, the structure has a 14β-hydroxy group in place of the amino group or possesses a trans-trans ring structure.

GENERAL DESCRIPTION OF INVENTION

The investigation carried out by the inventors indicates that, for each class of pregnane or androstane steroid, there are members with comparable potencies in the receptor binding assay. Accordingly, each of the classes of steroids is capable of yielding glycoside derivatives with typical digoxin-like (cardiac glycoside-like) actions on the heart as well as on other tissues, including the kidney.

Differences in toxicity, i.e. the tolerance to increasingly-greater dosage levels before the onset of arrhythmia, exist among the various steroid glycosides. However, the aglycone, 14β-hydroxyprogesterone (i.e. a compound of type (c), with the C/D joint cis) elicits cardiostimulation in isolated heart muscle.

The various different steroids exhibit different affinities for the intracellular target which mediates cardiodepression, which appears to persist, to varying degrees, even in the cardiostimulant pregnanes and androstanes and their glycosides. The cardiodepressive component of the compounds becomes manifest only at high dosage levels, however, and appears to be responsible for the generally lower toxicity of the novel compounds, as compared to the cardiac glycosides, so that toxicity developing from the digoxin-like action is suppressed by the depressant action. In addition, non-cardiac effects, such as effects on the kidneys and other organs vary among the compounds.

It has been observed, for example, that β-D-glucoside of 14β-hydroxyprogesterone has a receptor potency which is approximately ten times that of the aglycone. In addition, intrarenal infusion of the glucoside leads to increased urine volume and, surprisingly, when compared to the cardiac glycosides, increased sodium excretion but little effect on potassium excretion.

High potency is advantageous, for example, in in vitro work where organic solvents are undesirable and for infusions into the renal artery for similar reasons.

One particular class of compounds to which the present invention is directed is C-3-glycoside derivatives of 14β-hydroxypregnanes. One preferred group of such compounds has the formula:

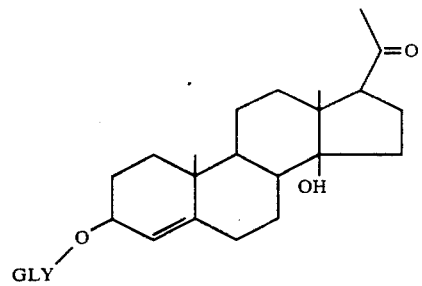

where GLY is a glycoside radical. Another preferred group of such compounds has the formula:

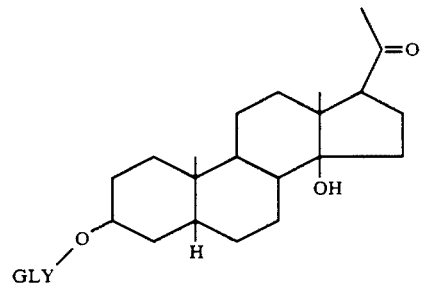

where GLY is a glycoside radical. Yet another preferred group of such compounds has the formula:

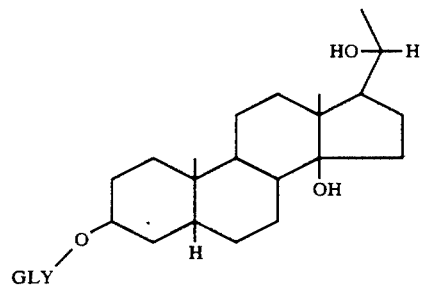

where GLY is a glycoside radical. An additional preferred group of compounds has the formula:

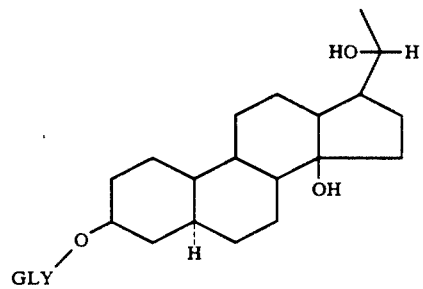

where GLY is a glycoside radical. A further preferred group of such compounds has the formula:

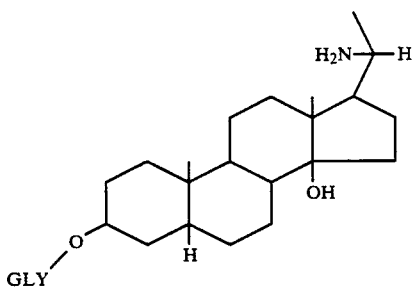

where GLY is a glycoside radical.

Another particular class of compounds to which the present invention is directed is C-3-glycoside derivatives of 17α-acetoxy-6α-methylpregnanes. One preferred class of such compounds has the formula:

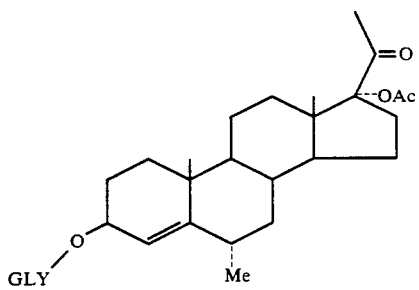

where GLY is a glycoside radical. Another preferred class of such compounds has the formula:

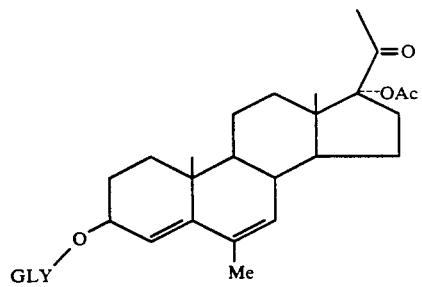

where GLY is a glycoside radical.

The sugar moiety in the glycoside derivatives of the present invention may be provided by any desired saccharide, which may be a monosaccharide, a disaccharide or a polysaccharide. Preferred glycoside radicals are β-D-glucoside, α-L-rhamnoside, and tridigitoxoside. The sugar moiety adds aqueous solubility to the steroid but also enhances binding and hence potency. The actual potency obtained may vary with the aglycone as well as with the saccharide employed. An example of the variation of potency with sugar moiety is the significant difference in potency observed for the glucoside and rhamnoside derivatives of 3β,14,20β-trihydroxy-5β,14β-pregnane (see data presented in Example 5 below). Routes to synthesis of the novel glycoside derivatives of the invention have been devised. Such derivatives vary in the nature of the sugar moiety at the C3- carbon, which may be β-D-glucose, α-L-rhamnose or other glycoside, the stereochemistry of the A/B ring junction, which may be unsaturated, 5α or 5β, and the function at the C-20 carbon, which may be >C=O, 20β(R)-ol, 20α(S)-ol or 20β-(R)NH$_2$.

Figure 5:
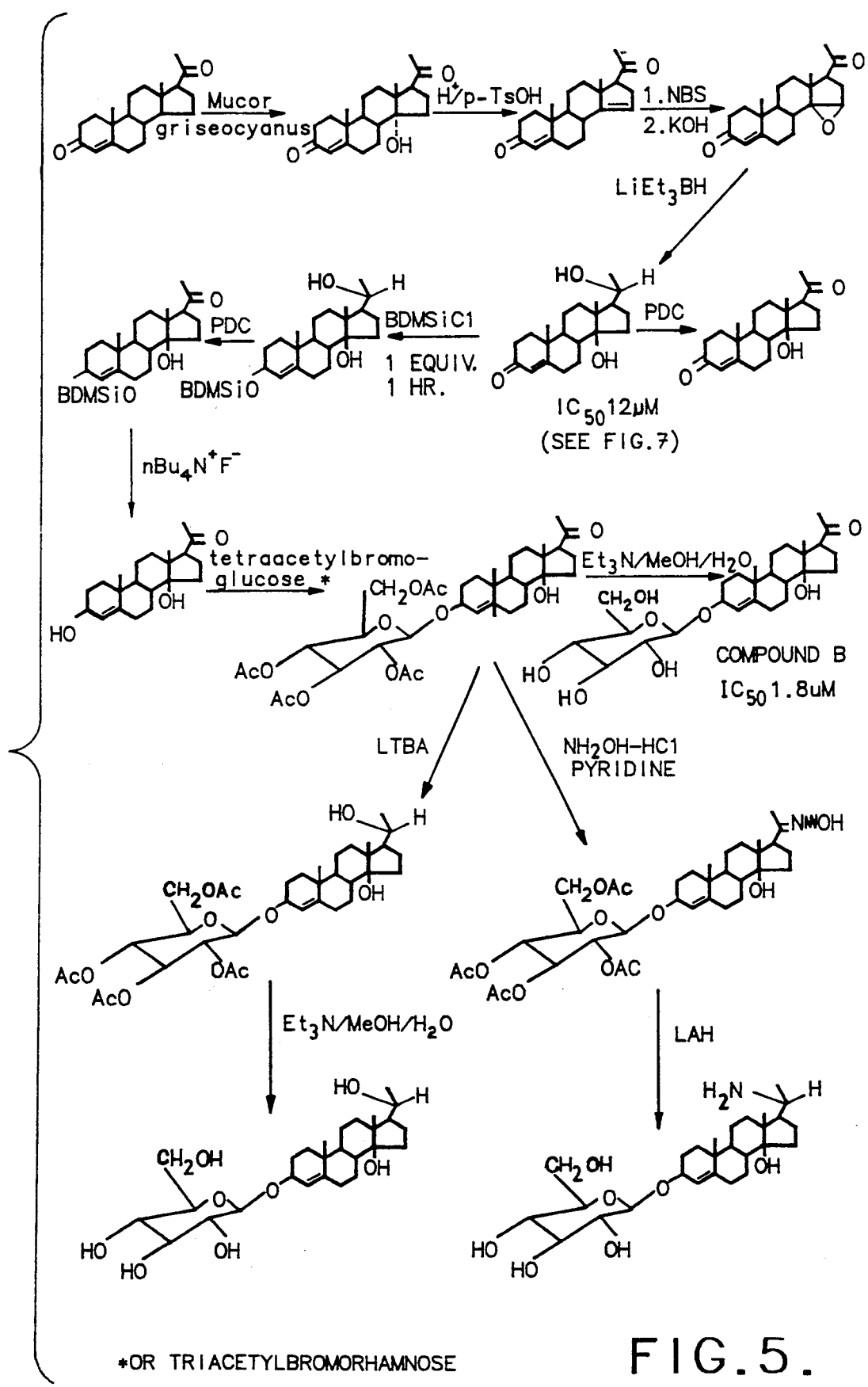
FIGS. 5, 6 and 7 are schematic outlines for forming various steroid glycoside derivatives with the 14β-hydroxyprogesterone and 14β-hydroxypregnane structure.
Figure 6:
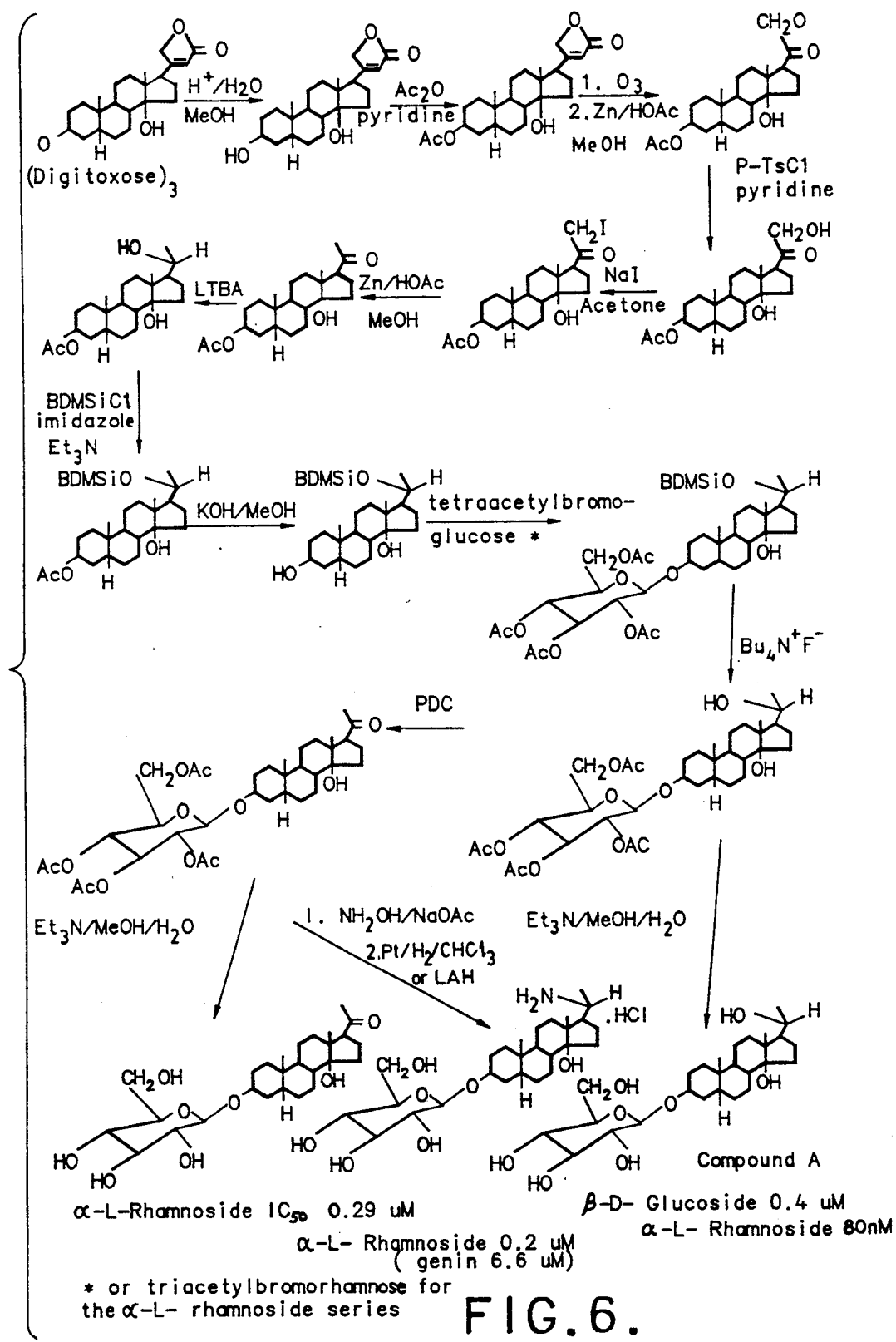

Synthetic schemes for obtaining these products are shown in FIGS. 5 to 8. FIG. 5 illustrates the provision of the C3-glucoside derivative of 14β-hydroxyprogesterone ("compound B") as well as the corresponding rhamnoside, and FIG. 6 illustrates the provision of the C3-glucoside derivative of 3β,14,20β-trihydroxy-5β,14β-pregnane ("compound A").

Figure 7:
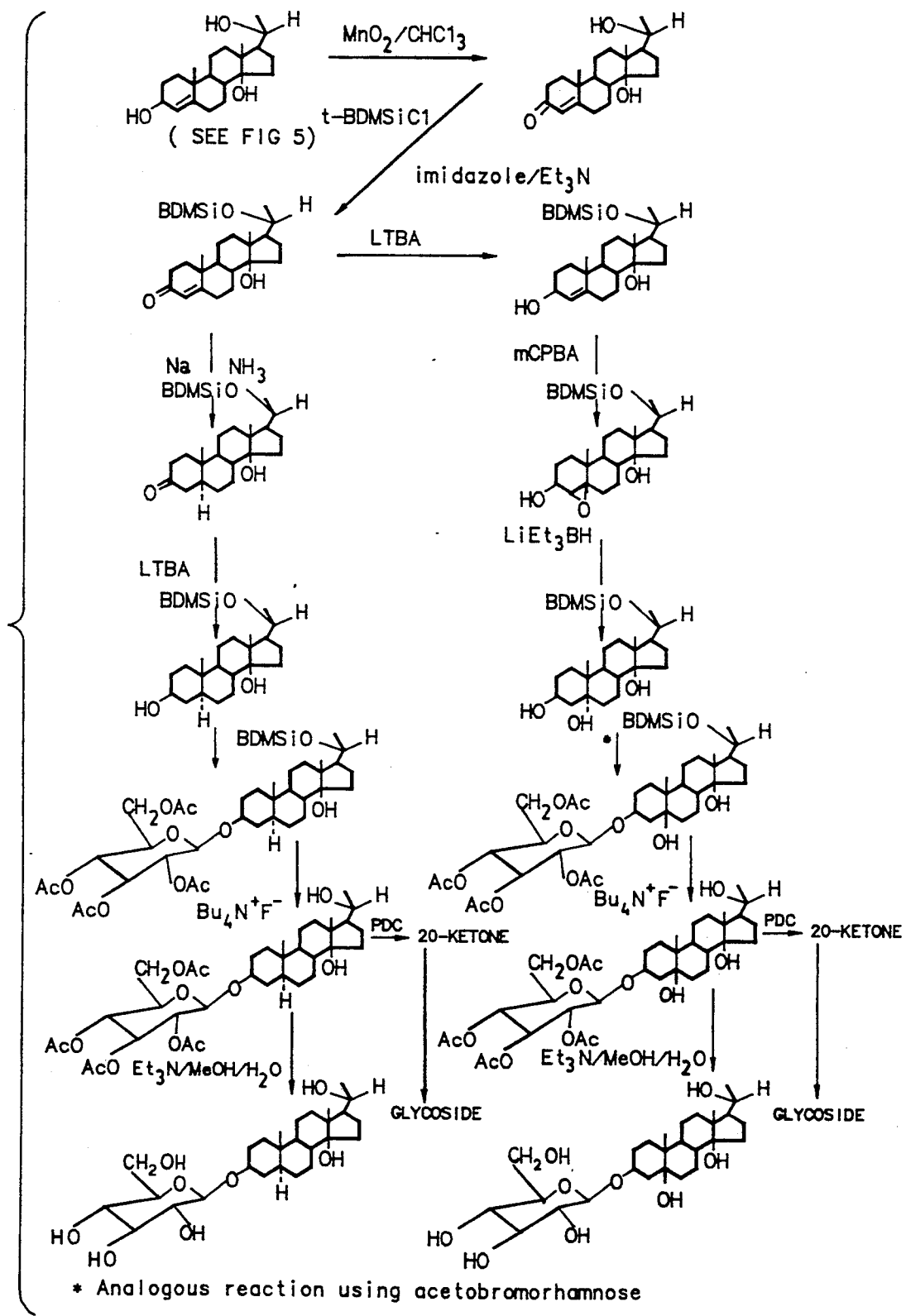
Figure 8:
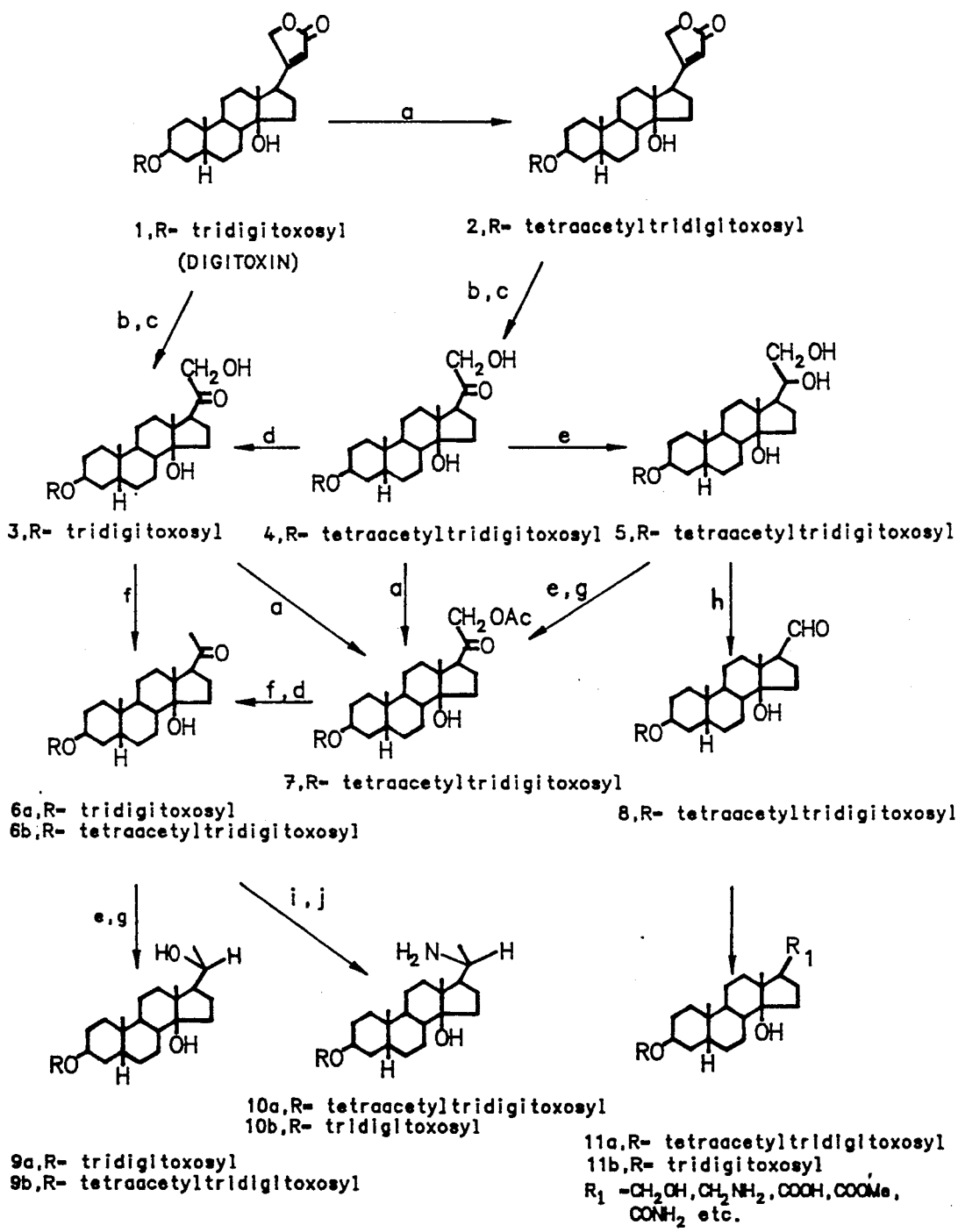
FIG. 8 is a schematic outline of the preparation of various C-17 derivatives of digitoxin.

FIG. 6 also illustrates details of how the corresponding 20β-amine derivative to compound A and the glucoside and rhamnoside derivatives of 3β,14-dihydroxy-5β,14β-pregnane-20-one. FIG. 7 shows the preparation of glucoside derivatives of various modifications to the C-5 site. Similar procedures may be employed to form the 17α-acetoxy-6α-methyl pregnane compounds. FIG. 8 shows the preparation of various C-17 derivatives of digitoxin. These tridigitoxose derivatives may be hydrolysed by dilute acid to the corresponding bis- and mono-digitoxose derivatives, as described by D. Satoh et al, Chem. Pharm. Bull. 18: 94 to 99, 1970, for the cardenolides.

In all these synthetic procedures, any other convenient glycoside derivative may be formed by substituting the appropriate saccharide, such as α-L-rhamnose, for the glucose, as indicated in the Figures.

Certain of the experimental data reported herein has already been published in the literature by the inventors and their coworkers, or is in press to be published. The applicants refer, in this regard, to the following publications:

(1) "Endogenous Digitalis: Current Status and Progesterone Derivatives as Candidates" by LaBella et al Proc. West. Pharmacol. Soc. 30:365 to 371 (1987);

2) "Progesterone Derivatives that Bind to the Digitalis Receptor: Synthesis of 14β-Hydroxyprogesterone" by Templeton et al, J. Med. Chem. 30, 1502 to 1505 (1987);

3) "14β-Hydroxyprogesterone Binds to the Digitalis Receptor, Inhibits the Sodium Pump and Enhances Cardiac Contractility" by Bose et al, Br. J. Pharmacology, 93:453 to 461 (Feb. 1988);

4) "Structure-Activity-Relationships of Progesterone Derivatives that Bind to the Digitalis Receptor: Modifications in A and B Rings" by Templeton et al, Steroid, May-June 1987 edition (published April 1988);

5) "Digitalis-like Pregnanes Cardiac and Renal Effects of a Glycoside of 14β-Hydroxyprogesterone" by Templeton et al, Can. J. Physical. Pharmacol., 66, 1420 to 1428 (1988); and 6) "Cardiac Glycoside-like Structure and Function of 5β,14β-Pregnanes" by Templeton et al, J. Med. Chem., 32, 1977 to 1981 (1989).

EXAMPLES

Binding studies were carried out in a $^3$H-ouabain radioligand binding assay (RBA) generally as described by Chow et al in Br. J. Pharmac. (1979), 67, 345 to 352. The results obtained are set forth in the Examples below:

Example 1

This Example provides receptor potency data for 14β-hydroxypregnane derivatives.

3β,14-Dihydroxy-5β,14β-pregnan-20-one (compound 1 in FIG. 2) shows significant binding (20 uM) to the cardiac receptor of heart muscle in the RBA which is only slightly altered on 3β-acetylation (2, 5.7 uM) but decreased on oxidation to the C-3 ketone (3, 60 uM). These results indicate absence of a strong hydrogen bond interaction between the 3β-alcohol and the receptor.

Replacement of the C-17 acetyl group by a C-17 oxo function (i.e. conversion to the androstane series) shows a decrease in binding in both the 3β-acetate (4, 60 uM) and the 3β-alcohol (5, 330 uM). The decreased activity of the C-17 oxo derivative is also consistent with hydrogen bonding, possibly through a water bridge, to a receptor atom.

Alternatively, introduction of C-4 unsaturation (compare FIG. 2, 3) increased binding strongly (6,10 uM) and a further increase occurs on formation of the 3β-alcohol (7, 3.8 uM), which was again increased on formation of the 3β-D-glucoside (8, 1.8 uM), whereas the 3β-succinate (9, 71 uM) decreased binding. The corresponding rhamnoside exhibited further increased potency with respect to the glucoside (0.29 uM for the rhamnoside).

Reduction of the C-20 ketone to the 20β-alcohol (10,36 uM) decreases binding in this case. Both 17α-pregnane epimers (11,12) of 1 and 10 were not active in the binding assay, indicating obstruction from the receptor on the α-face at C-17. The 14β,15β-epoxide (13, 135 uM) showed much weaker binding activity compared with the 14β-alcohol (6, 10 uM).

The change, therefore, from group (d) to group (c) (see FIG. 1) through C-4 unsaturation enhances binding. Besides the stereochemical changes, introduction of C-4 unsaturation introduces the possibility of π-bond electronic interactions capable of inducing changes in the conformation of the receptor. The importance of the C-4 unsaturation also was observed in the 17α-acetoxypregnane series (see Example 2 below). The further increase resulting from glucosidation and rhamnosidation correlates with greater water solubility, although that factor alone is insufficient to achieve greater binding in the 3β-succinate.

The importance for cardiac receptor binding of the C/D ring stereochemistry is demonstrated by comparison of 14β-hydroxyprogesterone (6, 10 uM) and 14α-hydroxyprogesterone (14, NA). However, the intermediate stereochemistry of progesterone (15, 60 uM) itself (14α) and 4,14-pregnadiene-3,20-dione (16, 134 uM) also show a measurable binding activity.

Example 2

This Example provides receptor potency data for 17α-acetoxypregnane derivatives.

Figure 3:
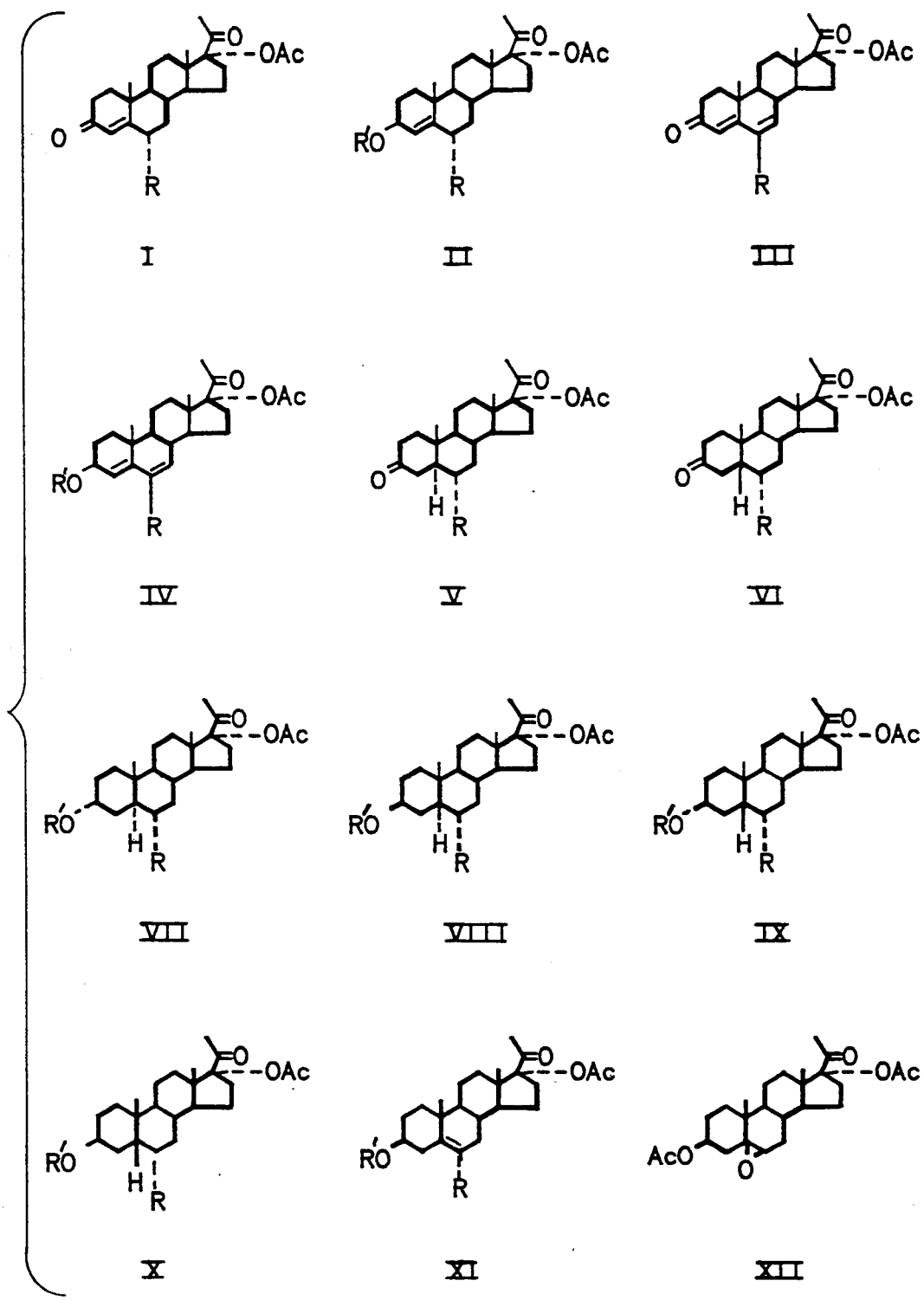
FIG. 3 shows examples of additional steroid structures of the classes of ring structure shown in FIG. 1.

A number of progesterone derivatives, having a 17α-acetoxy group and various functions at C-3 and C-6, interact at the cardiac glycoside (CG) binding site, as measured by the RBA with membranes from dog myocardium. Experimental values are given in the Table of FIG. 4 and structures in FIG. 3. The inventors have carried out structure-activity studies concerned with modification of the A and B rings as they influence potency in the RBA. As may be seen from the data, some progesterone derivatives with 5α- or 5β-stereochemistry show receptor competing activity. Among the congeners, highest potency is associated with the presence of C-4 or C-4,6-unsaturation and a C-6 substituent (CH3, Cl, Br). The C-3 function may be carbonyl, 3β-hydroxy, 3β-acetoxy or β-D-glucoside when associated with C-4 or C-4,6 unsaturation. In compounds with other substituents that promote activity, C-6α-substitution with —CH3, —Cl or —Br strongly enhance activity, —F, —OCH3, carbonyl or the unsubstituted compound promotes weak binding, and —OC2H5, —OAc, —OCOOCH3 or —OH eliminates binding activity. Receptor interaction with the double bond at C-4, but not C-5, appears to be particularly important for binding.

Figure 2:
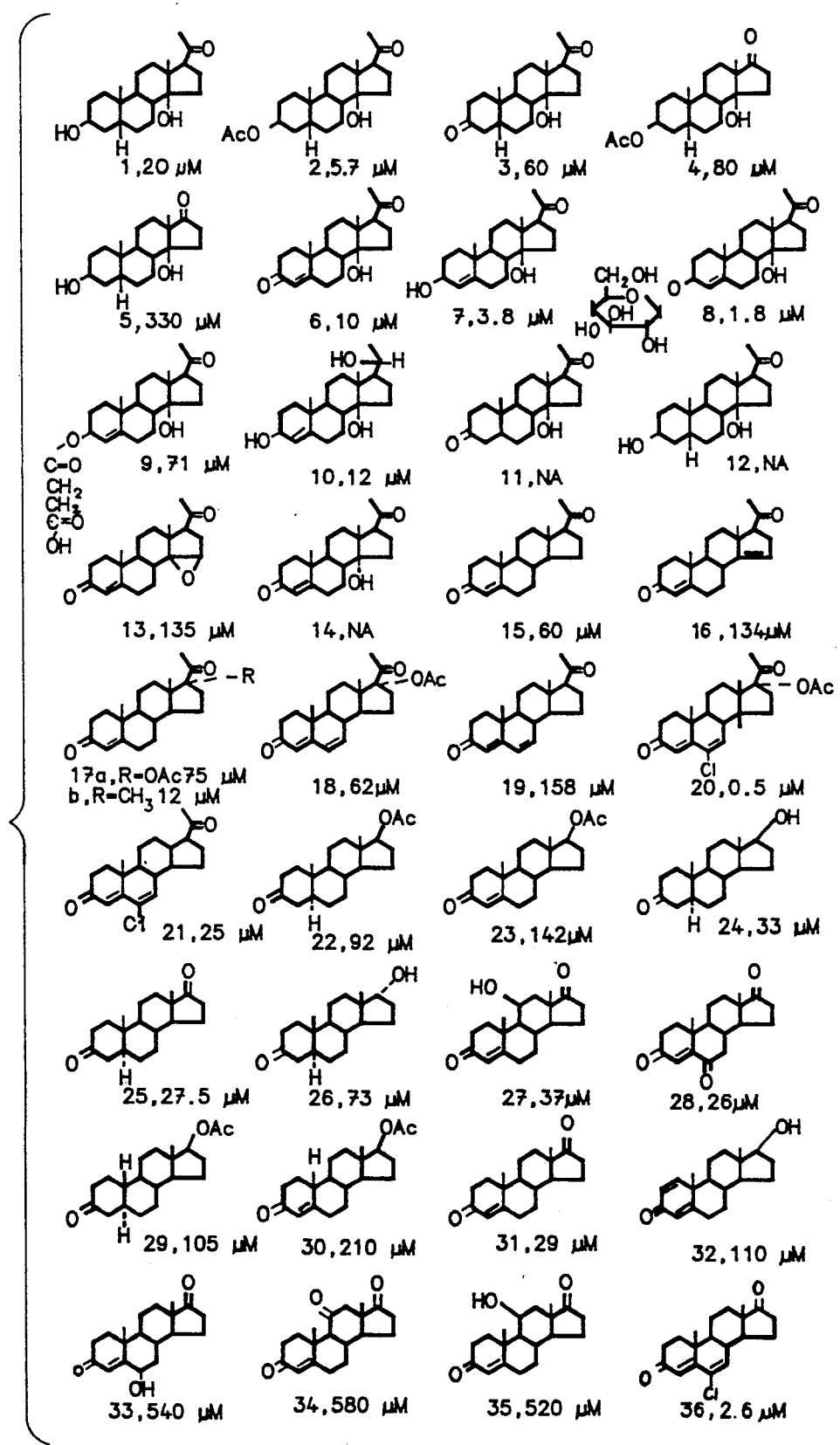
FIG. 2 shows examples of steroid structures of the classes of ring structure shown in FIG. 1, along with their ouabain displacement activity.

The most potent analog identified thus far is chlormadinone acetate (17α-acetoxy-6-chloropregna-4,6-diene-3,20-dione), which has 1/20 the potency of ouabain in the RBA. The 17α-acetoxy group (FIG. 2, 17a, 75 uM) is not essential to displacement activity as shown by the 17α-methyl derivative (FIG. 2, 17b, 12 uM).

Removal of the 17α-acetoxy function generally caused a decrease in binding activity. Although progesterone (15, 60 uM) and 17α-acetoxyprogesterone (17a, 75 uM) showed little difference activity was halved in the 4,6-dienes (18, 62 uM) and 19, 158 uM). Activity for chlormadinone acetate (20, 0.5 uM) was sharply reduced on removal of the 17α-acetoxy group (21, 25 uM).

Example 3

This Example provides receptor potency data for androstane and estrane derivatives.

We have also demonstrated that 5α and C-4 unsaturated derivatives of androstane (e.g. FIG. 2, compounds 22, 23, 24, 25, 26, 27, 28) and estrane (e.g. FIG. 2, compounds 29, 30) interact with the cardiac receptor indicating that the C-10 methyl group is not essential to binding.

5α-Androstane-3,17-dione (25, 27.5 uM) shows moderate displacement activity in the RBA which is essentially unaltered on introduction of a C-4 double bond (31, 29 uM). Introduction of a second double bond to give C-1, C-4 unsaturation (32, 110 uM) decreases displacement activity. Addition of a C-6 oxo (28, 26 uM) group to androst-4-ene-3,20-dione causes no change in displacement whereas a 6β-hydroxyl group (33, 340 uM) greatly decreases binding. In contrast, addition of a C-11 oxo group (34, 588 uM) or a C-11α-alcohol (35, 520 uM) strongly decreases binding whereas the C-11β-alcohol (27, 33 uM) causes no significant change suggesting an interaction around C-11. However, conversion to 6-chloroandrost-4,6-diene-3,17-diene (chlormidine acetate analog) provides the most potent derivatives (see FIG. 2, compound 36).

Example 4

This Example describes the preparation and properties of a novel 3β-D-glucoside derivative of 14β-hydroxyprogesterone (14β-OHP-glu) and its properties.

The aglycone 3β,14-dihydroxy-14β-pregn-4-en-20-one was prepared from 14β-hydroxyprogesterone by utilizing the scheme outlined in FIG. 5.

In this scheme, regioselective reaction of the isomeric intermediate triol mixture with 1.3 equivalents of t-butyldimethylsilyl chloride (TBDMSiCl) for one hour produced tee siloxy derivative. Neutral oxidation with pyridinium dichromate (PDC) results in the formation of the 20-ketone. Desilylation with tetrabutylammonium fluoride (TBAF) in THF gave the epimeric 3-hydroxy mixture, from which the aglycone was separated and crystallized. The reaction sequence was carried out without the isolation of the individual intermediates because of the presence of sterioisomers.

Reduction of 14β-hydroxyprogesterone with lithium tri-t-butoxyaluminum hydride gave more rapid reduction of C-20 and, therefore, could not be used to prepare compound. The attachment of β-D-glucose at C-3 was achieved using the procedure of Brown et al with Fetizon's reagent (see Arzneim. Forch./Drug Res. 1981, 31, 1959). The glucoside had a melting point of 220° to 222° C.

In an ($^3$H)ouabain binding assay in which the ouabain measured 14 nM, 14β-OHP-glu had an IC$_{50}$ of 1.8 uM and is about 10 times more potent than the aglycone (3.8 uM). The 5β(H), 14β(OH) analog of progesterone is weaker than 14β-hydroxyprogesterone but is cardiostimulant.

14β-OHP-Glu consistently causes positive inotropic response in mutated canine, ventricular, trabeaclae muscle in a dose dependent manner. High concentrations elicit a biphasic contractile response, an initial increase followed by a decrease. During the peak inotropic response and subsequent depression, it is possible to elicit spontaneous after contraction(s) by rapid electrical stimulation of the muscle, which is similar to the toxic responses of the digitalis compounds.

The effects of an intrarenal infusion of ouabain and 14β-hydroxyprogesterone glucoside were compared. Both compounds increased urine volume. Ouabain produced a marked increase in potassium excretion with little or no change in sodium excretion. On the other hand, 14β-OHP-glu increased sodium excretion significantly but had no influence on potassium excretion. This marked natriuresis and absence of kaliuresis by the cardiotonic pregnane has practical clinical implications.

Example 5

The β-D-glucoside and the α-L-rhamnoside derivatives of 3β,14,20β-trihydroxy-5β,14β-pregnane were prepared following the preparative procedure set forth in FIG. 6. Detail of the procedure for preparation of the α-L-rhamnoside derivative and the characterization of the products are set forth below. Potency testing revealed the following results:

| β-D-glucose derivative ("compound A") | 0.4 uM |
| α-L-rhamnose derivative | 80 nM |

14,20β-Dihydroxy-3β-(α-L-rhamnopyranosyloxy)-5β,14β-pregnane (see FIG. 6)

To a stirred solution of 20β-t-butyldimethylsilyloxy-3β, 14-dihydroxy-5β,14β-pregnane (see FIG. 6) (420 mg) in dichloromethane (60 ml) was added Fetizons reagent (10 g) and, over 10 minutes, a solution of triacetoxybromorhamnose (2.55 g) in dichloromethane (30 ml). After 3 hours the reaction mixture was washed thoroughly with sodium hydrogen carbonate, water, dried over sodium sulfate and evaporated to give a residue which was dissolved in tetrahydrofuran (50 ml) and treated with tetra-n-butlyammonium fluoride (352 mg) for 16 hours, water was added and the mixture extracted with ether to give a product which was dissolved in methanol (20 ml), triethylamine (20 ml) and water (2 ml) and allowed to stand at room temperature for 72 hours under argon. The reaction mixture was evaporated to dryness and the residue dissolved in methanol and placed on silica gel (20 g) and the solvent allowed to evaporate. The silica gel was washed with petroleum ether (30/60) and dichloromethane. Elution with 8-10% methanoldichloromethane gave fractions of the α-L-rhamnoside (FIG. 6) (170 mg) recrystallized from methanol-water to give (81 mg) mp 243°-246° C. $^1$H nmr (CDCl$_3$:CD$_3$OD, 1:1) δ:0.95,(19CH$_3$), 0.97, S(18CH$_3$), 1.27, DD, J=6.2Hz(6'CH$_3$), 2.27,S(21CH$_3$), 2.96,dd, J=4.1,9.3Hz(17αH), 3.40,t, J=9.5Hz(4'H), 3.64–3.76, m(3'H and 5'H), 3.82,dd,j=1.7, 3.3 Hz (2'H), 3.95, s, w½ 7 Hz (3H), 4.30, s(ROH), 4.80, d, J=1.5 Hz (1'H)ppm; $^{13}$C nmr (CDCl$_3$:CD$_3$OD,1:1) δ:31.0$^a$(1), 27.0$^b$(2), 72.6$^c$(3), 30.3$^a$(4), 37.5(5), 27.2$^b$(6), 22.1$^d$(7), 40.6(8), 35.7(9), 35.8 (10), 21.3$^d$(11), 39.7(12), —(13), 86.2(14) 34.3(15), 25.4(16), 63.0(17), 15.5(18), 24.1(19), 219.4(20), 33.1(21), 98.8(1'), 72.0$^c$(2'), 72.0$^c$(3'), 73.4$^c$(4'), 69.0(5'), 17.7(6') ppm. Anal. C 65.87; H, 9.63 C$_{27}$H$_{46}$O$_7$.½H$_2$O requires C, 65.96; H, 9.64.

Example 6

The α-L-rhamnoside derivative of 3β,14-dihydroxy-20β-amino-5β,14β-pregnane was prepared following the preparative procedure set forth in FIG. 6, together with the aglycone (20β-amino-3β,14β-dihydroxy-5β,14β-pregnane hydrochloride). Potency testing revealed the following results:

| α-L-rhamnose derivative | 0.2 uM |
| aglycone | 6 uM |

Example 7

The β-D-glucoside derivative of 17α-acetoxy-3β-hydroxy-6α-methylpregn-4-en-20-one was prepared following the procedure set forth in FIG. 5 for the corresponding derivative of 3β,14β-dihydroxy-14β-pregn-4-en-20-one (see below). Potency testing revealed the following results:

| β-D-glucoside | 3.3 uM |

The effect of intravenal infusion of the glucoside was studied. The compound exhibited sodium excreting and potassium sparing similar to the results observed for 14β-hydroxyprogesterone-3-glucoside (see Example 4).

17α-Acetoxy-6α-methyl-3-β-[β-D-(glucopyranosyl-)oly]-pregn-4-en-20-one

To a stirred solution of 17α-acetoxy-3β-hydroxy-6α-methylpreg-4-en-20-one (1 g) in dichloromethane (100 ml) was added molecular sieves (4A, 3 g) and Fetizon's reagent (13.5 g), followed by red mercuric oxide (500 mg) and mercuric bromide (500 mg). 1-Bromo-2,3,4,6-tetraacetyl-β-D-glucopyranose (6.25 g) in dichloromethane (25 ml) was divided into two portions, one of 15 ml and the other of 10 and each were added through a funnel over 30 min., at an interval of 0 and 3 hour respectively. The reaction solution was stirred under argon in the dark for 15 hours.

The solution was filtered through a pad of Celite and the filtrate was evaporated to dryness to give a syrupy residue. The residue was dissolved in a mixture of methanol (75 ml), triethylamine (50 ml) and water (5 ml). The solution was stirred under argon for 3 days and then evaporated to give a residue (1.4 g). The residue was purified through a flash column chromatography over silica gel (20 g). The fractions from the elution with 4% methanol in dichloromethane were collected to give a crystalline product (225 mg) (16% yield).

Recrystallization from methanol-water gave the pure glucoside (185 mg), m.p. 228°-229° C. $^1$H nmr (CDCl$_3$:CD$_3$OD, 1:1), δ: 0.65 (s, 1H, $^{13}$CH$_3$), 1.03 (d, 3H, J=6.4 Hz, (6 CH$_3$), 1.07 (s, 3H, 10CH$_3$), 2.05 (s, 3H, C17—OCOCH$_3$), 2.12 (S, 3H, 20CH$_3$), 2.90 (t, 1H, C16βH) 3.20-3.40 (m, 4H, 2'H, 3'H, 4'H and 5'H), 3.80 (dq, 2H, 6'H), 4.28 (t, 1H, 3αH), 4.45 (d, 1H, 1'H, J=7.5 Hz), 5.42 (s, 1H, 4'H) ppm. $^{13}$C nmr (CDCl$_3$:CD$_3$OD; 1:1) δ: 36.41(1), 27.44(2), 76.79(3), 118.90(4), 151.57(5), 33.03(6), 42.37(7), 36.32(8), 54.68(9), 38.15(10), 21.24(11), 31.72(12), 47.56(13), 51.83(14), 24.27(15), 30.84(16), 97.63(17), 14.71(18), 19.04(19), 206.07(20), 26.65(21), 127.031(COCH$_3$), 21.27(COCH$_3$), 19.90(6αCH$_3$), 102.76(1'), 74.27(2'), 77.24(3'), 70.90(4'), 77.28(5'), 62.33(6') ppm.

Example 8

The α-L-rhamnose derivative of the C-20 oxime of 3β,14-dihydroxy-5β,14β-pregnane-20-one was prepared following the procedure set forth in FIG. 6. Potency testing revealed the following results:

| α-L-rhamnose/oxime | 0.15 uM |
| --- | --- |

Example 9

This Example describes the preparation and characteristics of 14,21-dihydroxy-3β-tridigitoxosyloxy-5β,14β-pregnan-20-one (FIG. 8,3) and its potency data.

Digitoxin (206 mg) in CH$_2$Cl$_2$ (100 ml) and EtOAc (50 ml) was cooled to −50° C. in a dry-ice-acetone bath and ozone passed through the solution for 45 min when a persistent blue color appeared indicating excess reagent was present. Tlc (2% MeOH—CH$_2$Cl$_2$) showed no starting material. Nitrogen gas was passed through the solution to remove excess ozone. To the clear solution was added zinc dust (1 g) and acetic acid:methanol (1:1) (5 ml). After stirring at −50° C. for 1½ hours, the mixture was brought to room temperature, filtered and the organic layer washed thoroughly with water, excess aqueous sodium hydrogen carbonate, dried over anhydrous sodium sulfate, filtered and evaporated to dryness. The residue was chromatographed on silica gel (Merck Type 60 H for tlc) using the dry chomatography method and eluted first with hexanes, ether-hexanes and acetone-hexanes mixtures. Elution with 2% acetone-hexanes gave fractions which on two recrystallizations gave the 21-hydroxyketone (FIG. 8,3) (37 mg) m.p. 216°-218° C. from methanol-water. $^1$H nmr (CDCl$_3$:CD$_3$OD; 1:1)δ:0.93, 0.94 (C10 and C13CH$_3$) 1.22-1.28 three overlapping doublets J=6 Hz (6', 6'', 6'''CH$_3$), 2.84, dd, J=3.9, 9.74Hz (17 H), 3.32, m(4', 4'', 4'''H), 3.34, br s(ROH), 3.82, m(5', 5'', 5'''H), 4.90, m(1', 1'', 1'''H) ppm; $^{13}$C nmr (CDCl$_3$:CD$_3$OD; 1:1) δ: 30.31$^a$(1), 26.99$^b$(2), 73.26$^c$(3), 30.74$^a$(4), 36.98$^d$(5), 27.09$^b$(6), 21.30(7), 40.57(8), 35.83$^d$(9), 35.67(10), 22.06(11), 39.52(12), under solvent (13), 86.12(14), 34.34(15), 25.24(16), 57.90(17), 15.39(18), 23.99(19), 2 18.81(20), 70.08(21), 18.25, 18.32, 18.37 (6, '6, ''6'''), 37.50, 37.86, 38.57 (2', 2'', 2'''), 67.11, 67.30, 68.26, 68.73, 68.87, 70.24, 73.50$^c$, 82.86, 83.16(3', 3'', 3'''; 4', 4'', 4'''; 5', 5'', 5'''), 95.97, 99.42, 99.60 (1', 1'', 1''') ppm.

Potency data revealed the following results:

| 3Θ-tridigitoxoside (FIG. 8, 3). | 2 uM |
| --- | --- |

Example 10

This Example describes the preparation and characteristics of 3β-tridigitoxosyloxy-14-hydroxy-5β,14β-pregnan-20-one (FIG. 8, 6) and its potency data.

The hydroxyketone tridigitoxoside(FIG. 8,3) (91 mg) was stirred in acetic acid (10 ml) containing zinc dust (4 g) for 6 hrs at room temperature. After filtration and addition of water, extraction with ether gave on recrystallation from methanol-water the α-methylketone tridigitoxoside (FIG. 8, 6) (30 mg) m.p. 245°-247° C. $^1$H nmr(CDCl$_3$:CD$_3$OD,1:1) δ:0.95 and 0.96 (18 and 19 CH$_3$), 1.25, m (6', 6'', 6'''CH$_3$), 2.26(20CH$_3$), 2.95, dd, J=4 and 9 Hz (17H), 3.22, m(4', 4'', 4'''H), 3.83, m(5', 5'', 5'''H), 4.03, m(3'H and 3αH), 4.17, br s (ROH), 4.25, m, two (dd/3' and 3''H), 4.92, m(1', 1'', 1'''H) ppm. $^{13}$C nmr (CDCl$_3$:CD$_3$OD, 1:1)δ: 30.34(1), 27.02$^a$(2), 73.3$^b$(3), 30.76(4), 37.03(5), 27.13$^a$(6), 22.06$^c$(7), 40.59(8), 35.70(9), 35.86(10), 21.3$^c$(11), 39.75(12) under solvent (13), 86.22(14), 34.29(15), 25.39(16), 63.00(17), 15.55(18), 24.03(19), 219.43(20), 33.16(21), 95.98, 99.44, 99.62 (1', 1'', 1'''), 37.53, 37.89, 38.61(2', 2'', 2'''), 67.13, 67.33, 68.29, 68.76, 68.90, 70.27 (3', 3'', 3'''; 5', 5'', 5'''), 82.89, 83.20(4', 4''), 73.61$^a$(4'''), 18.29, 18.36, 18.41 (6', 6'', 6''')ppm.

Potency data revealed the following results:

| 3β-tridigitoxoside (FIG. 8,6) | 1.3 μM |
| --- | --- |

Example 11

This Example illustrates the preparation and characterization of 14,20β-dihydroxy-3β -tridigitoxosyloxy-5β,14β-pregnane (FIG. 8) and its potency data.

The α-methylketone (FIG. 8, 6) (94 mg) was dissolved in dry tetrahydrofuran (25 ml) and lithium tri-tert-butoxyaluminohydride (400 mg) added. The mixture was stirred at room temperature for 18 hrs when no starting material remained by tlc (4% MeOH/CH$_2$Cl$_2$). Excess acetone was added followed by water. Extraction with dichloromethane: ether (1:2) followed by washing the organic layer with water, aqueous sodium hydrogen carbonate, brine, filtration and evaporation gave a residue which was recrystallized from chloroform/acetone to give the 20β-alcohol (FIG. 8) (36 mg), m.p. 203°-205° C.

$^{13}$C nmr δ: 30.63$^a$(1), 27.32$^b$(2), 73.98$^c$(3), 31.08$^a$(4), 37.40(5), 27.57$^b$(6), 22.22$^d$(7), 41.20(8), 36.01(9), 36.49(1,0), 21.36$^d$(11), 42.31(13), under solvent (1,3), 86.27(14), 32.55(15), 26.98$^b$(16), 57.31(17), 16.89(18), 24.32$^e$(19), 72.13(20), 23.53$^e$(21), 96.27,99,77, 99.95(1', 1'', 1'''), 37.85, 38.21, 38.93(2', 2'', 2'''), 67.46, 67.67, 68.60, 69.06, 69.19, 70.56 (3', 3'', 3''' and 5', 5'', 5'''), 18.55, 18.63, 18.67 (6', 6'', 6''') ppm.

Potency data revealed the following results:

| 3β-tridigitoxoside (FIG. 8). | 0.6 μM |
| --- | --- |

SUMMARY OF DISCLOSURE

In summary of this disclosure, the present invention provides novel steroids and glycoside derivatives thereof having digoxin-like activity, as well as synthesis schemes for the preparation thereof. Modifications are possible within the scope of this invention.

What we claim is:

1. A C3-glycoside derivative of a 14β-hydroxypregnane and having the formula:

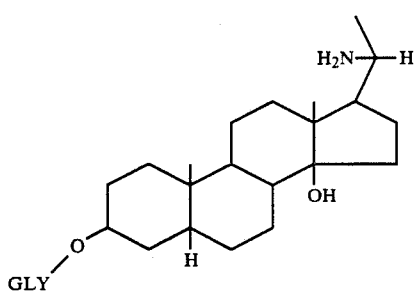

wherein GLY is a glycoside radical selected from the group consisting of glucoside, rhamnoside and tridigitoxoside.

2. A C3-glycoside derivative of a 14β-hydroxypregnane and having the formula:

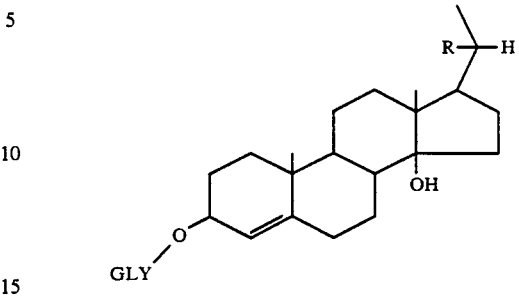

where GLY is a glycoside radical selected from the group consisting of glucoside, rhamnoside and tridigitoxoside and R is an amino group.

* * * * *